(12) United States Patent
So et al.

(10) Patent No.: US 8,098,376 B2
(45) Date of Patent: Jan. 17, 2012

(54) INTEGRATED EMBEDDED PROCESSOR BASED LASER SPECTROSCOPIC SENSOR

(75) Inventors: Stephen So, Houston, TX (US); Gerard Wysocki, Princeton, NJ (US); J. Patrick Frantz, Tokyo (JP); Frank K. Tittel, Houston, TX (US)

(73) Assignee: William Marsh Rice University, Houston, TX (US)

( * ) Notice: Subject to any disclaimer, the term of this patent is extended or adjusted under 35 U.S.C. 154(b) by 456 days.

(21) Appl. No.: 12/440,373

(22) PCT Filed: Oct. 6, 2006

(86) PCT No.: PCT/US2006/039282
§ 371 (c)(1),
(2), (4) Date: Apr. 24, 2009

(87) PCT Pub. No.: WO2008/030250
PCT Pub. Date: Mar. 13, 2008

(65) Prior Publication Data
US 2010/0177316 A1    Jul. 15, 2010

Related U.S. Application Data

(60) Provisional application No. 60/824,843, filed on Sep. 7, 2006.

(51) Int. Cl.
*G01N 21/00* (2006.01)
(52) U.S. Cl. ......... 356/432; 356/433; 356/441; 356/442
(58) Field of Classification Search ........... 356/432–444
See application file for complete search history.

(56) References Cited

U.S. PATENT DOCUMENTS 3,609,317 A * 9/1971 Siebert, Jr. .................. 702/76
4,163,382 A   8/1979 Amer
4,267,732 A * 5/1981 Quate ........................... 73/606
(Continued)

FOREIGN PATENT DOCUMENTS
WO   2008030250 A2   3/2008
(Continued)

OTHER PUBLICATIONS

ALTAIR(TM) Bid Specification, "Pro single-gas detector," Aug. 2006, 3 pages, ALTAIR Pro.
(Continued)

*Primary Examiner* — Gregory J Toatley
*Assistant Examiner* — Jarreas C Underwood
(74) *Attorney, Agent, or Firm* — Conley Rose, P.C.; Rodney B. Carroll

(57) ABSTRACT

A novel low-power and compact laser spectroscopic sensor is described herein. Embodiments of the disclosed sensor utilize state-of-the-art microprocessors and digital processing techniques to reduce power consumption and integrate functions into a small device. In particular, novel software methods are disclosed which allow the use of low-power microprocessors which draw no more than about 0.02 W of power. Such low-power enables long battery life and allows embodiments of the sensor to be used in portable applications. In addition, the system architecture and methods described in this disclosure allow a single integrated embedded processor to control all the subsystems necessary for a laser spectroscopic sensor further reducing sensor size and power consumption. In addition, a power efficient method of calibrating a photoacoustic laser spectroscopic sensor is disclosed.

10 Claims, 2 Drawing Sheets

U.S. PATENT DOCUMENTS

| | | | |
|---|---|---|---|
| 4,321,832 A * | 3/1982 | Runyan | 73/708 |
| 4,443,887 A * | 4/1984 | Shiramizu | 377/110 |
| 4,699,518 A * | 10/1987 | Tanabe | 368/75 |
| 4,817,413 A | 4/1989 | Asano et al. | |
| 4,862,342 A * | 8/1989 | Dhyanchand et al. | 363/40 |
| 5,309,160 A * | 5/1994 | Powell et al. | 342/128 |
| 6,298,096 B1 * | 10/2001 | Burgin | 375/296 |
| 6,539,411 B1 * | 3/2003 | Johnson | 708/271 |
| 6,975,402 B2 * | 12/2005 | Bisson et al. | 356/432 |
| 7,012,696 B2 | 3/2006 | Orr et al. | |
| 7,015,733 B2 * | 3/2006 | Giuroiu | 327/156 |
| 7,245,380 B2 | 7/2007 | Kosterev | |
| 7,248,611 B2 | 7/2007 | Kosterev et al. | |
| 7,291,856 B2 * | 11/2007 | Haran et al. | 250/574 |
| 2002/0093658 A1 | 7/2002 | Han | |
| 2006/0044562 A1 | 3/2006 | Hagene et al. | |

FOREIGN PATENT DOCUMENTS

| | | | |
|---|---|---|---|
| WO | 2008030250 A3 | 3/2008 | |

OTHER PUBLICATIONS

AppliedSensor borchure entitled "Air quality module," http://www.appliedsensor.com/products/air_quality_module.html, Aug. 16, 2006, 2 pages, AppliedSensor.

AppliedSensor borchure entitled "Carbon monoxide sensor," undated by admitted to be prior art, 2 pages.

AppliedSensor Technologies, http://www.appliedsensor.com/technologies/, Aug. 18, 2006, 1 page, AppliedSensor.

Foreign communication from a related counterpart application—International Preliminary Report on Patentability, PCT/US2006/039282, Mar. 17, 2009, 6 pages.

Foreign communication from a related counterpart application—International Search Report and Written Opinion, PCT/US06/39282, Jul. 11, 2008, 8 pages.

Frish, Michael B., et al., "Extended performance handheld and mobile sensors for remote detection of natural gas leaks," Phase II Final Report, May 2005, 87 pages, Physical Sciences Inc. and U.S. Department of Energy.

McNesby, Kevin L., et al., "Diode laser-rased sensor for fast measurement of binary gas mixtures," Apr. 27-29, 1999, pp. 191-200, Halon Options Technical Working Conference.

Provisional patent application entitled "Integrated single embedded processor based laser spectroscopic sensor," by Stephen So, et al., filed Sep. 7, 2006 as U.S. Appl. No. 60/824,843.

So, Stephen G., et al., "Development of digital signal processor controlled quantum cascade laser based trace gas sensor technology," Sensors Journal, Jan. 17, 2006, pp. 1-17, IEEE.

So, Stephen G., et al., "Ultra-compact, high efficiency, quartz-enhanced photoacoustic spectroscopy based trace gas sensor platform," 2006, pp. 292-293, IEEE.

Von Drasek, W., et al., "Laser-based multiple gas sensor system for the metals processing industry," http://www.industrialheating.com/CDA/Archives/, Jan. 10, 2003, 6 pages.

* cited by examiner

INTEGRATED EMBEDDED PROCESSOR BASED LASER SPECTROSCOPIC SENSOR

CROSS-REFERENCE TO RELATED APPLICATIONS

This application is a filing under 35 U.S.C. §371 of International Application No. PCT/US2006/039282 filed Oct. 6, 2006 by Stephen So, et al. and entitled "Integrated Embedded Processor Based Laser Spectroscopic Sensor," which claims priority to U.S. Provisional Patent Application 60/824,843 filed Sep. 7, 2006 by Stephen So, et al. and entitled "Integrated Single Embedded Processor Based Laser Spectroscopic Sensor," both of which are incorporated herein by reference in their entirety.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD OF THE INVENTION

This invention relates generally to the field of laser based spectroscopy. More specifically, the invention relates to an integrated, low-power, laser spectroscopic sensor.

BACKGROUND

There are several widely used laser spectroscopy techniques which involve measurement of absorption of the laser light within a sample. In order to achieve high sensitivity in many cases the measurement signals have to be extracted from noisy background. This usually involves phase sensitive detection of the modulated laser radiation. PAS (photoacoustic spectroscopy) is an analytical method that involves stimulating a sample with modulated light and detecting the resulting sound waves emanating from the sample. A photoacoustic measurement can be made as follows. First, light is used to excite molecules within a sample. Such excitation can include, for example, absorption of the light by the molecule to change an energy state of the molecule. As a result, the energized molecule enters an excited state. Optical excitation is followed by energy transfer processes (relaxation) from the initially excited molecular energy level to other degrees of freedom, in particular translational motion of the fluid molecules. During such relaxation, heat, light, volume changes and other forms of energy can dissipate into the environment surrounding the molecule. Such forms of energy cause expansion or contraction of materials within the environment. As the materials expand or contract, sound waves are generated.

In order to produce sound waves, or photoacoustic signals, the light is modulated at a specific acoustically resonant modulation frequency f (having a modulation period 1/f), sometimes also referred to herein as ω. The sample environment can be enclosed and may be constructed to resonate at the modulation frequency. An acoustic detector mounted in acoustic communication with the sample environment can detect changes occurring as a result of the modulated light excitation of the sample. Because the amount of environmental change associated with the absorbed energy is proportional to the concentration of the absorbing molecules, the photoacoustic signal can be used for concentration measurements.

In typical PAS, a resonant acoustic cavity or sample cell is used to isolate and amplify sound wave signals, thereby increasing sensitivity of detection. The light intensity or wavelength is modulated at a frequency, f. The absorbed energy is accumulated in the acoustic mode of the sample cell during oscillation periods. Quartz enhanced photoacoustic laser spectroscopy (QEPAS) has been found to be highly sensitive and selective technique for the detection of gas concentrations at the parts-per-billion (ppb) and parts-per-trillion (ppt) level. Because of its sensitivity, QEPAS may be useful in many different applications. A number of applications, however, require an ultra-compact footprint i.e. small size, and low power consumption.

Currently, systems are based on modular architectures with an externally mounted laser source, separate power and thermal controllers, environmental transducers, and/or separate processing hardware and software. Such systems require human feedback to operate and may not be considered to be truly integrated. In addition, at present, sensors typically utilize separate sub-system controllers running independently. Systems with independent sub-systems, as such, cannot be considered fully integrated. Because each sub-system requires a respective controller, present systems are bulky, expensive, and require impractical amounts of electrical power.

Consequently, there is a need for a fully integrated trace-gas sensor platform which is low cost, compact, and power efficient.

SUMMARY

A novel low-power and compact laser spectroscopic sensor is described herein. Embodiments of the disclosed sensor utilize state-of-the-art microprocessors and digital processing techniques to reduce power consumption and integrate functions into a small device. In particular, novel software methods are disclosed which allow the use of low-power microprocessors which draw no more than about 0.02 W of power. Low power consumption enables long battery life and allows embodiments of the sensor to be used in portable applications. In addition, the system architecture and methods described in this disclosure allow a single integrated embedded processor to control all the subsystems necessary for a laser based spectroscopic sensor further reducing sensor size and power consumption.

These and other needs in the art are addressed in one embodiment by a laser spectroscopic sensor for detecting a compound comprising a detector capable of transmitting a signal in response to absorption of light by the compound. The laser spectroscopic sensor further comprises a light source having a modulation frequency. The light source introduces a beam of light to said acoustic detector. The laser spectroscopic sensor also comprises a microprocessor coupled to said light source and said acoustic detector. In addition, the laser spectroscopic sensor comprises software executable on said microprocessor. The software causes said microprocessor to control the temperature, wavelength, and modulation frequency of said light source. The software also causes the microprocessor to acquire and process data from said detector. Additionally, the software causes the microprocessor to generate a first waveform having a first frequency. The first waveform is divisible into a plurality of different waveforms and each waveform has a frequency which is a multiple of the modulation frequency of said light source.

In a further embodiment, the detector is an acoustic detector having a resonant frequency. The software executable on the microprocessor causes the microprocessor to iteratively generate the first waveform to tune the modulation frequency of said light source to the resonant frequency of said acoustic detector.

In another embodiment, a method for calibrating a laser spectroscopic sensor comprising an acoustic detector, a lock-in amplifier, and a light source having a modulation frequency, comprises (a) generating a first waveform having a first frequency. The first waveform has a first frequency greater than twice the modulation frequency of said light source. Moreover, the method comprises (b) forming a plurality of synchronized waveforms from the first waveform, wherein each synchronized waveform is different. Furthermore, the method comprises (c) tuning the reference frequency of the first lock-in amplifier and the modulation frequency of the light source with the plurality of synchronized waveforms. Additionally, the method comprises (d) determining whether the modulation frequency of the light source is tuned to a harmonic resonant frequency of the acoustic detector. If modulation frequency of the light source is not tuned to a harmonic resonant frequency of the acoustic detector, the method comprises (e) adjusting the first frequency. The method further comprises f) repeating steps (a) through (e) until the modulation frequency of the light source is tuned to the resonant frequency of the acoustic detector so as to calibrate the laser spectroscopic sensor.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

Figure 1:
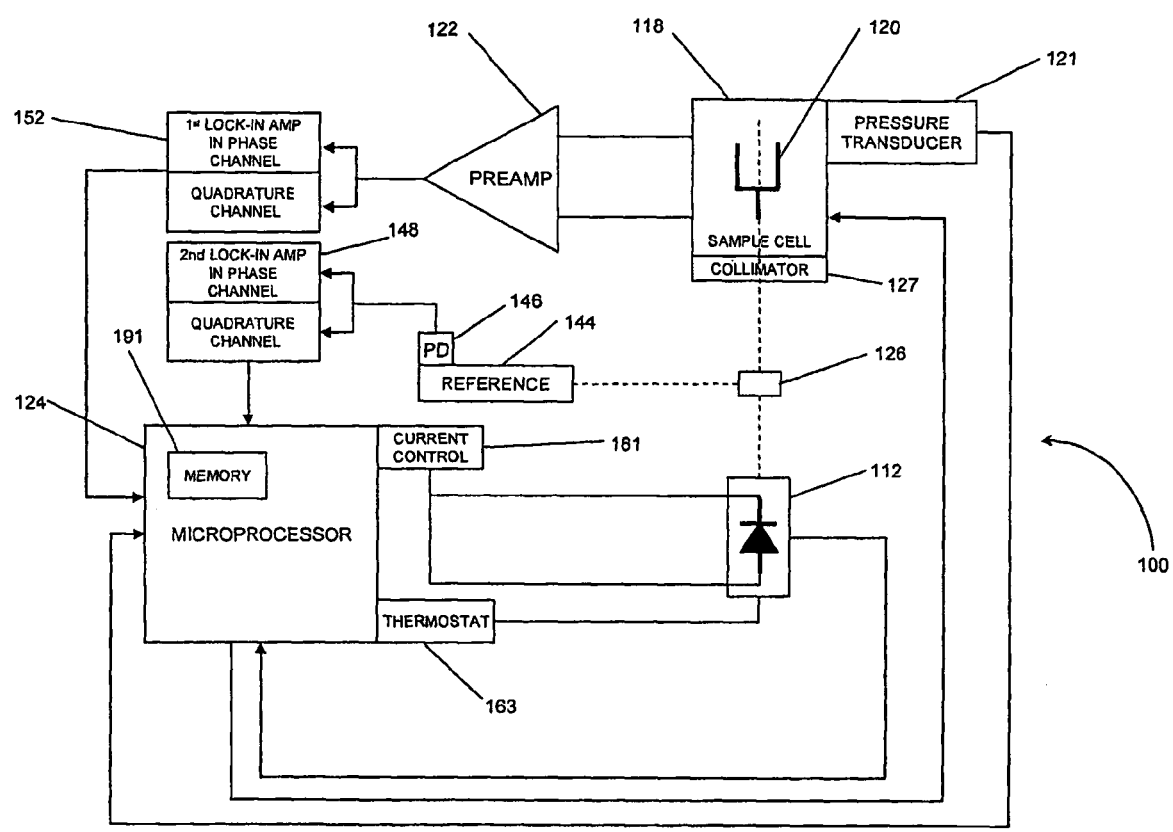
FIG. 1 illustrates an embodiment of an integrated laser spectroscopic sensor.

FIG. 1 illustrates an embodiment of a photoacoustic laser sensor. The methods disclosed herein here may be extended to any modulation based laser spectroscopy such as photodetector-based laser spectroscopy. In an embodiment, a laser spectroscopic sensor is configured to apply a modulated light signal to a sample and to detect the resulting acoustic signal using a phase-locked detector such as a lock-in amplifier. By way of example, reference is made to FIG. 1, in which a laser spectroscopic sensor 100 comprises a light source 112 configured to emit a beam of radiation into a sample cell 118. According to at least one embodiment, all elements of laser spectroscopic sensor 100 are mounted on a small footprint circuit board. Light source 112 typically comprises a laser. However, any light source capable of emitting a modulated beam of light may be used. In a preferred embodiment, light source is a near infra-red semiconductor diode laser. Other examples of suitable lasers that may be used include without limitation, lead salt diode lasers, quantum cascade and inter-band cascade lasers, fiber lasers, solid-state lasers, other semiconductor lasers, or gas lasers. Filters (not shown) may be provided between light source 112 and sample cell 118 if desired.

Laser spectroscopic sensor 100 generally comprises a sample cell 118 which encloses a detector 120 and contains a sample compound of interest. However, in some embodiments, laser spectroscopic sensor 100 comprises detector 120 without sample cell 118. Sample cell 118 may be a multipass cell or any other absorption chamber if using a non-photoacoustic method. Sample cell 118 can comprise a number of materials known to persons of ordinary skill in the art, and preferably comprises a sample compound substantially transparent to the wavelength(s) of light emanating from light source 112. Preferred sample compounds for sample cell 118 will accordingly vary depending on the wavelengths of light utilized in the spectroscopic apparatus. Sample compound may be a fluid or a gas and may substantially fill sample cell 118. Sample compound can, for example, comprise a gas stream in which it is desired to detect the presence of a contaminant gas or impurity. Thus, in some embodiments, sample cell 118 includes a pump (not shown) to adjust flow of a sample into sample cell 118. In an embodiment, a pressure sensor 121 such as a resistive bridge pressure transducer is coupled to sample cell 118 to measure the pressure within sample cell 118. In addition, other sensors may be coupled to sample cell 118 to measure temperature, pH, etc.

The detector 120 may be mounted within sample cell 118 and in acoustic communication with a sample. Detector 120 preferably comprises an acoustic transducer such as, for example, a piezoelectric element or a microphone and is mounted such that a sample compound is provided between a surface of detector 120 and sample cell 118. In the embodiment shown, detector 120 comprises a quartz tuning fork. However, the detector 120 may comprise any suitable piezoelectric or resonant crystal material. In alternative embodiments (not shown), detector 120 can be any type of detector (e.g. photodetector) capable of detecting the absorption of light by a compound. Detector 120 may be mounted on the inside or outside wall of sample cell 118. Detector 120 is typically removably mounted into sample cell 118. In an embodiment, detector 120 additionally comprises a resonator (not shown) to further amplify the acoustic signal from detector 120. The resonator is typically cylindrical in configuration, but may comprise any suitable geometry. Typically, sample cell 118 also comprises a collimator 127 to focus the beam of light to detector 120.

Detector 120 is in electrical communication with a preamplifier 122, which is preferably in electrical communication with a first lock-in amplifier 152. Preamplifier 122 is used to convert and amplify the signal from detector 120 to the appropriate level for detection by first lock-in amplifier 152. In an embodiment, preamplifier 122 is a transimpedance preamplifier. Lock-in amplifiers are well-known in the art and typically comprise a low pass filter and a phase-sensitive detector. Both lock-in amplifiers 148 and 152 are preferably integrated into the laser spectroscopic sensor. As such, any lock-in amplifiers or other demodulation devices known in the art may be used with embodiments of the sensor. First lock-in amplifier 152 is coupled to microprocessor 124. In certain embodiments, microprocessor 124 processes the amplified signal from first lock-in amplifier 152 as described in further detail below.

In a further embodiment, laser spectroscopic sensor 100 comprises a reference cell 144. Reference cell 144 generally contains a reference concentration of the target compound of interest. Typically, a photodetector 146 is coupled to reference cell 144. However, any device may be coupled to reference cell 144 to detect absorption. Photodetector 146 senses the absorption by the reference concentration in reference cell 144. Photodetector 146 is also in electrical communication with a second lock-in amplifier 148. In some embodiments, a preamplifier (not shown) may be disposed between photodetector 146 and second lock-in amplifier 148. Both first and second lock-in amplifiers 152, 148 are preferably dual phase lock-in amplifiers.

A beam splitter 126 may be included in the sensor and can be configured to facilitate division of the through beam of light. Beam splitter 126 splits the light signal into a first and second beam, where first beam is directed at sample cell and second beam is directed at reference cell. In further embodiments, beam splitter 126 splits beam into more than two beams. Beam splitter 126 may be any suitable device known in the art.

In a preferred embodiment, the sensor 100 comprises a single microprocessor 124 such as a low-power digital signal processor. For example, the microprocessor 124 may be a MSP430-class DSP processor commercially available from Texas Instruments, Inc. However, any suitable microprocessors may be used with the laser spectroscopic sensor. Other examples of suitable processors include without limitation, field programmable gate arrays, microcontrollers, programmable logic devices, application specific integrated circuits and the like. The microprocessor 124 controls all the subsystems or functions of the laser spectroscopic sensor 100 including without limitation, diode laser temperature control, diode laser current control, sample gas temperature, sample gas pressure, signal conditioners, waveform generation, etc. It is preferred that all sub-system controls of the laser spectroscopic sensor are integrated on a single microprocessor. Integration of all controls in a single microprocessor eliminates the need for a bulky external controlling device such as a computer, or external control hierarchy. In addition, using a single microprocessor 124 consumes less power and reduces complexity in the laser spectroscopic sensor 100. However, it is contemplated that additional embodiments of the laser spectroscopic sensor 100 may utilize more than one microprocessor.

In embodiments, microprocessor 124 includes memory 191. Memory 191 may comprise volatile (e.g., random access memory) and/or non-volatile memory (e.g., read only memory (ROM), electrically-erasable programmable ROM (EEPROM), Flash memory, etc.). In a preferred embodiment, memory 191 is flash memory. Memory 191 may be used to store data or code (e.g., software, discussed below) that is executed by the microprocessor 124. The executable code may be executed directly from the non-volatile memory or copied to the volatile memory for execution therefrom. Laser spectroscopic sensor 100 may also include memory external to microprocessor 124. This external memory is generally coupled to microprocessor 124 and may comprise either volatile or non-volatile memory.

In another embodiment, a plurality of frequency dividers (not shown) are coupled to microprocessor 124. As defined herein, a frequency divider is any module or circuit which divides a waveform or signal into a lower frequency waveform or signal. In a preferred embodiment, the plurality of frequency dividers are asynchronous counters. However, the frequency dividers may comprise other types of frequency dividers known in art. The frequency dividers are used to divide the waveform generated by microprocessor 124 as will be described in more detail below.

It is contemplated that many sensing devices or modules may be in electrical communication with microprocessor 124 to form multiple control loops. For example, in further embodiments, a current controller module 161 and a thermoelectric module 163 are in electrical communication with microprocessor 124. Current controller module 161 and thermoelectric module 163 are also in electrical communication with light source 112. Microprocessor 124 controls current controller 161 to adjust current of light source in response to changes in resonant frequency of detector. Current controller module 161 is also responsible for adjusting the central wavelength and the wavelength modulation of light source 112. Thermoelectric module 163 controls the temperature of light source since temperature affects the frequency of the light signal emitted from light source. In certain embodiments, a temperature sensor (not shown) is coupled to light source 112 which transmits temperature data to microprocessor 124.

According to one embodiment, the microprocessor draw less than about 0.05 W, more preferably less than about 0.02 W. Low power consumption is an important aspect of the laser spectroscopic sensor 100, as the less power is used or drawn from microprocessor, the longer the sensor may be used in portable applications. Thus, in preferred embodiments, the sensor 100 is powered by a battery such as a lithium ion battery (not shown).

Microprocessor 124 may be coupled to a variety of different communication devices (not shown). In an embodiment, microprocessor 124 is coupled to an RF or wireless antenna. Alternatively, microprocessor 124 is coupled to a wireless chip. In addition, microprocessor 124 may be coupled to a communications port such a Universal Serial Bus Port, a serial port, a parallel port, Firewire port, etc. In another embodiment, the laser spectroscopic sensor 100 includes input devices allowing a user to input parameters for using laser spectroscopic sensor 100. The input devices may be coupled to microprocessor 124 to program microprocessor or adjust laser spectroscopic sensor 100 parameters. Example of input devices include without limitation, keypads, jumpers, touch sensors, and buttons.

In a preferred embodiment, the laser spectroscopic sensor 100 including all of its individual modules (e.g. detector, microprocessor, light source, etc.) is mounted or is capable of fitting on a single circuit board. Thus, another novel feature of the disclosed sensor 100 is its ultra-compact size. It is envisioned that embodiments of laser spectroscopic sensor 100 will be no larger than a personal digital assistant or a portable MP3 player, thus, allowing placement of many such sensors 100 in remote locations. In general, laser spectroscopic sensor 100 including light source 112, microprocessor 124, and all other electronics consumes no more than 5 W of power, preferably no more than 1 W of power.

In operation, a beam of light is generated by light source 112 according to a signal from microprocessor 124 and is passed through sample cell 118 to excite the molecules within the sample compound in sample cell 118. The microprocessor 124 generally provides a reference electrical signal in the form of a sine wave or rectangular wave synchronized to the light modulation. Nonradiative decay or molecular rearrangements cause expansions and/or contractions of a material within sample cell 118 to generate acoustic waves passing from sample to detector 120. In photoacoustic embodiments, detector 120 detects the resulting acoustic waves and passes signals corresponding to, for example, gas pressure changes in the acoustic waves to first lock-in amplifier 122. Alternatively, detector 120 is a photodetector which measures the intensity of the beam of light after absorption by the sample compound. The change in intensity is proportional to the concentration of the target compound in the sample.

Both first and second lock-in amplifiers 152, 148 generally comprise two channels and produces two outputs (DC voltage levels, X and Y) corresponding to in-phase and quadrature (e.g. 90 degrees), components of the detector signal with respect to the reference signal. However, the lock-in amplifiers 152, 148 may also be single channel amplifiers. The signal from first lock-in amplifier 152 is then sent to microprocessor 124 for acquisition and processing. An output device may be coupled to sensor 100 (not shown) and be configured to convert information obtained from microprocessor 124 to, for example, a graphical or numerical display.

As mentioned above, beam splitter 126 divides the beam of light into a first beam and second beam, in which second beam is directed at reference cell 144. Reference cell 144 contains a reference concentration of the target compound to be measured. Photodetector 146 provides a signal at the wavelength at which the target compound absorbs the light. The signal is relayed through second lock-in amplifier to detect the wavelength error. The wavelength error measurement is then sent to microprocessor 124. Microprocessor 124 performs a computation on the wavelength error signal, and sends this error factor to current controller 161 to adjust the wavelength of light source 112. This feedback loop ensures that the light source 112 is emitting light at the appropriate wavelength corresponding to the absorption line of the target compound. This wavelength control is also known as "line-locking." In additional embodiments, microprocessor controls the wavelength modulation of light source 112 via current controller module 161.

In a further embodiment, software executable on microprocessor 124 allows for data acquisition and processing from detector 120. As microprocessor 124 receives a signal from detector 120 via first lock-in amplifier 152, the software instructs microprocessor to store the signal level in memory 191. The software also enables microprocessor 124 to calculate the concentration of the target compound in the sample using the acquired data (i.e. signal level). Furthermore, the software may instruct microprocessor to send the calculated concentration to an output device through any communications devices coupled to microprocessor 124 such as a USB port or wireless chip.

In embodiments utilizing an acoustic detector, software executable on the microprocessor 124 matches the modulation frequency of the light source 112 and the lock-in amplifier frequencies with the resonant frequency of the detector 120. The resonant frequency of the detector 120 is variable because of changes in temperature and pressure in the sample chamber 118. In order to maximize the signal from the detector 120, the modulation frequency of the light source 112 is tuned to match the resonant frequency of the detector 120. In addition, the lock-in amplifiers 152, 148 are tuned or programmed to the detector resonant frequency in order to amplify only signals at the detector's resonant frequency. A power-efficient and novel method for performing the aforementioned calibration is described below.

Figure 2:
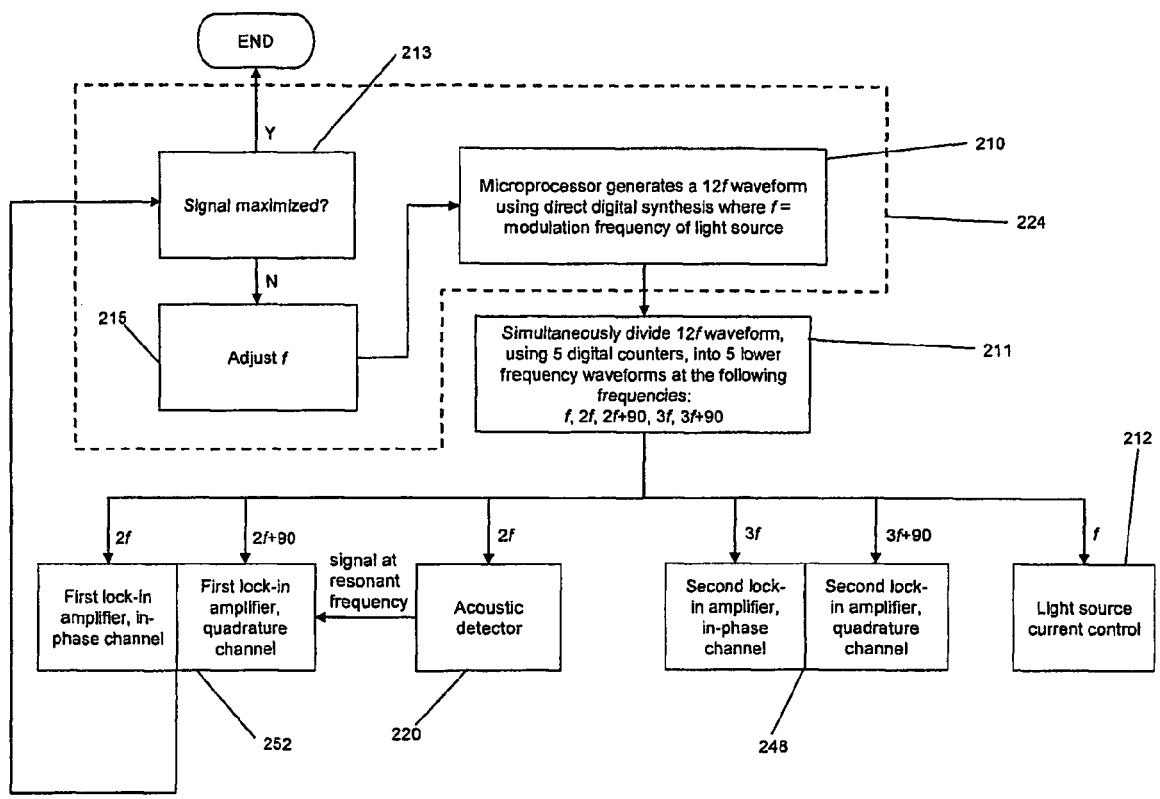
FIG. 2 illustrates an embodiment of a method for calibrating a laser spectroscopic sensor.

As shown in FIG. 2, in a preferred embodiment, the software causes the microprocessor 224 to periodically calibrate or tune the modulation frequency of the light source to the resonant frequency of an acoustic detector 220. In an embodiment, the software causes the microprocessor to check the resonant frequency every 1 minute to 20 minutes, preferably 10 minutes. However, the period between frequency calibrations or tunings may be any suitable time period. In an embodiment, the software causes the microprocessor to calibrate the resonant frequency continuously. Referring now to FIG. 2, to begin the calibration process, the microprocessor synthesizes or generates a first waveform that is divisible into a plurality of different waveforms at lower frequencies in block 210. Furthermore, the software may cause the microprocessor to shut off light source during the calibration or tuning process. In a preferred embodiment, microprocessor 224 generates a waveform that is divisible into 5 lower frequency waveforms. Typically, f is initially the modulation frequency of the light source from the previous calibration. According to at least one embodiment, the first waveform has a frequency of 12f. However, waveforms of any suitable frequency may be generated.

In at least one embodiment, the software causes the microprocessor 224 to generate the first waveform using a direct digital synthesis algorithm (DDS). However, any suitable methods may be used to synthesize the waveform such as programmable and controlled oscillators, direct-analog synthesis or indirect synthesis. The generated waveform is sent to a plurality of frequency dividers to divide the first waveform into a plurality of synchronized waveforms. That is, the plurality of waveforms may be formed in parallel (i.e. simultaneously) or with some other timing pattern. As mentioned above, the plurality of frequency dividers may be a plurality of digital counters. Other frequency dividers may also be used. Preferably, the 12 f waveform is sent to 5 different digital counters which divide it into 5 respective waveforms in block 211. In an embodiment, each of the 5 waveforms has one of the following frequencies: f, 2f, 2f+90 degrees, 3f, 3f+90 degrees, where f is the modulation frequency of light source 212. Alternatively, the first waveform may be divided into any waveform having a frequency that is a multiple of f (i.e. 2f, 3f, 4f, 5f, etc.).

The 2 f and 2f+90 degree waveforms are sent as reference signals to the reference and quadrature channels of the first lock-in amplifier 252, respectively. In addition, the 2f waveform signal may be sent to detector 220 to excite the acoustic detector 220 if laser excitation does not provide a strong enough signal. The 3f and 3f+90 degree waveforms are sent to the reference and quadrature channels of second lock-in amplifier 248, respectively. The f waveform is sent to the light source current controller where the modulation frequency is adjusted or tuned to match the detector resonant frequency. Therefore, the software executable on microprocessor 224 is optimized such that the only function for frequency calibration performed by the microcontroller 224 is to iteratively generate a first waveform divisible into the 5 specific waveforms. Accordingly, a novel aspect of the software is that a plurality of synchronized waveforms may be generated with minimal processing and power draw by microprocessor 224.

A preamplifier 122 converts the signal from the detector to sufficient voltage levels for the first lock-in amplifier 252 to detect. That signal is connected to the first lock-in amplifier 252. First lock-in amplifier 252 and light source 212 must be tuned to the resonant frequency of the detector in order to generate and amplify the signal from acoustic detector 220. If first lock-in amplifier 252 and light source 212 are not provided with the correct reference frequency, the signal from acoustic detector 220 will not be maximized. If microprocessor 224 determines that the signal from first lock-in amplifier 252 has not reached a maximum value in block 213, microprocessor 224 iterates another frequency in block 215 and generates another first waveform at this different frequency. This waveform is continuously divided by digital counters and sent to each respective module i.e. light source, lock-in amplifiers, etc.

The software causes the microprocessor 224 to continue iterating and generating new waveforms with different frequencies until microprocessor 224 determines that the signal from first lock-in amplifier 252 has reached a maximum value. In an embodiment, the software utilizes a binary search algorithm to determine whether the signal from lock-in amplifier 252 is maximized. Without being limited by theory, it is believed that once the signal from lock-in amplifier 252 is maximized the modulation frequency of light source 112 is matched with the resonant frequency of the acoustic detector 220. Once an amplified signal from the first lock-in amplifier 252 at the specific resonant frequency of the acoustic detector is detected by microprocessor 224, the software halts the tuning or calibration process. If the signal to noise ratio is high enough, the modulation frequency may itself be modulated and a lock-in amplifier may be used to lock in the resonant frequency.

Referring back to FIG. 1, in embodiments of laser spectroscopic sensor 100 utilizing a photodetector (not shown), the frequency of the first waveform generally is not iterated or adjusted. Instead, the microprocessor 124 is programmed to repeatedly generate a first waveform at a constant first frequency. For example, in embodiments of sensor 100 having first and second lock-in amplifiers 152, 148 and a photodetector, the first waveform is still divided into a plurality of different waveforms using a plurality of frequency dividers. Each waveform from the plurality of frequency dividers is sent to the respective channels of the lock-in amplifiers as well as light source control. However, the frequency of each of these waveforms does not change over time because the frequency of the first waveform remains constant. As a result, the disclosed techniques may increase the power efficiency for photodetection embodiments of the sensor 100 as only one waveform at a single frequency needs to be generated by the microprocessor 124. Nevertheless, it is contemplated that the calibration method for acoustic detectors described above may also be used with a photodetector if desired.

The software executable on microprocessor may further utilize pulse width modulation (PWM) to control individual sub-systems of laser spectroscopic sensor 100. In another embodiment, software executable on microprocessor causes the microprocessor to automatically perform PWM power conversion from a power supply for the light source or to use PWM to heat and cool the light source.

The cost effectiveness and low-power utilization of the disclosed sensor 100 allows for the application of many sensors as nodes in a wireless sensor network. The sensors may be integrated into common handheld devices with other functionality (e.g., cell phones or personal digital assistants (PDAs)) which may be used in self-diagnostic health applications or personal air quality control (helpful in urban or industrial environments).

A wireless network on the scale of hundreds of nodes would enable applications such as source localization for fire detection, or wide area monitoring for environmental applications. These sensors may also be capable of utilizing environmentally friendly energy sources (e.g. solar, wind, vibration), and work together to determine optimum duty cycles for each member of the network.

Although the present invention and its advantages have been described in detail, it should be understood that various changes, substitutions and alterations may be made herein without departing from the spirit and scope of the invention as defined by the appended claims.

What is claimed is:

1. A method comprising:
   generating a first waveform at a first modulation frequency using a direct digital synthesis (DDS) algorithm; and
   dividing the first waveform into a plurality of second waveforms at a plurality of second modulation frequencies using a plurality of frequency dividers,
   wherein the second modulation frequencies comprise a light source modulation frequency that is used to control the frequency of a light source, a first in-phase modulation frequency and a first quadrature modulation frequency that are used to detect absorption of a first portion of the light source by a sample compound, and a second in-phase modulation frequency and a second quadrature modulation frequency that are used to detect absorption of a second portion of the light source by a reference concentration of the sample compound, and
   wherein a frequency initially used to modulate the light source is equal to about f, wherein the first modulation frequency is equal to or greater than about 12f, wherein the light source modulation frequency is equal to about f, wherein additional timing waveforms comprise the first in-phase modulation frequency, the first quadrature modulation frequency, the second in-phase modulation frequency, and the second quadrature modulation frequency, wherein the first in-phase modulation frequency is equal to about 2f, wherein the first quadrature modulation frequency is equal to about 2f+90 degrees, wherein the second in-phase modulation frequency is equal to about 3f, and wherein the second quadrature modulation frequency is equal to about 3f+90 degrees.

2. The method of claim 1, wherein the first waveform is generated using a software that is executed on a processor.

3. The method of claim 2, wherein the processor is a fixed point digital signal processor.

4. The method of claim 3, wherein the frequency dividers are hardware timers that are part of the processor.

5. The method of claim 4 further comprising detecting at least one of the second waveforms using a lock-in amplifier comprising a filter and a phase sensitive detector.

6. The method of claim 5, wherein a transimpedence preamplifier is used to detect the second waveform, wherein the transimpedence preamplifier is coupled to the lock-in amplifier.

7. The method of claim 1, wherein dividing the first waveform into the second waveforms is repeated until a signal level for detecting absorption of the first portion of the light source by the sample compound reaches a limit.

8. An apparatus comprising:
a light source; and
a processor configured to implement a method comprising:
dividing a first waveform into at least a second waveform having a lower frequency; and
filtering the second waveform to create a sinusoid;
attenuating the sinusoid using control signals from the processor; and
controlling a current fed to the light source using the attenuated sinusoid, thereby controlling a modulation of a light emitted from the light source;
a detector;
an amplifier coupled to the detector and the processor,
wherein the amplifier receives a signal from the detector, performs phase sensitive detection of the signal, and passes the signal to the processor and wherein the processor, the light source, and the detector are mounted on a circuit board, and wherein the circuit board consumes a power less than about five watts (W);
a wireless transmitter coupled to the processor; and
a power source coupled to the circuit board,
wherein the processor produces data associated with emission or uptake of a chemical, and
wherein the wireless transmitter transmits the data to a central location.

9. The apparatus of claim 8, wherein the detector is an acoustic detector.

10. The apparatus of claim 8, wherein the detector comprises an absorption cell and a photodetector.

* * * * *